United States Patent [19]
Phalangas et al.

[11] Patent Number: 4,740,369
[45] Date of Patent: Apr. 26, 1988

[54] ULTRAVIOLET RADIATION ABSORBING COMPOSITIONS

[75] Inventors: Charalambos J. Phalangas; Leon W. Wright, both of Wilmington, Del.

[73] Assignee: ICI Americas Inc., Wilmington, Del.

[21] Appl. No.: 931,083

[22] Filed: Nov. 17, 1986

Related U.S. Application Data

[63] Continuation of Ser. No. 817,501, Jan. 9, 1986, abandoned.

[51] Int. Cl.[4] .................... A61K 7/025; A61K 7/027; A61K 7/42; A61K 7/48
[52] U.S. Cl. ............................................ 424/59; 106/3; 106/10; 424/47; 424/63; 424/64; 424/70; 514/844; 514/846; 514/937; 514/938
[58] Field of Search ................. 424/59; 549/498, 499, 549/501

[56] References Cited

U.S. PATENT DOCUMENTS 3,215,550 11/1965 Strobel et al. ................... 424/59 X
3,215,724 11/1965 Strobel et al. ................... 424/59 X
3,275,520  9/1966 Strobel et al. ....................... 424/59
3,475,421 10/1969 Chretien et al. ..................... 549/498
3,475,462 10/1969 Chretien et al. ..................... 549/498

FOREIGN PATENT DOCUMENTS 18097 9/1960 Japan ..................................... 424/59

OTHER PUBLICATIONS

Nakanishi et al., CA. 64, 14168e, (1966).
Thewalt et al., CA. 63, 6941f, (1965).
Usmanov et al., CA. 63, 1941f, (1965).
Usmanov et al., CA. 76, 72830n, (1972).
Tsizin et al., CA. 83, 73,399r, (1975).
Kushwaha et al., CA. 67, 64,219u, (1967).
Schiller et al., CA. 83, 15655e, (1975).

Primary Examiner—Dale R. Ore

[57] ABSTRACT

Sunscreen compositions are described which comprise a carrier having incorporated therein in an amount effective to provide protection against the harmful effects of ultraviolet radiation a compound of the formula:

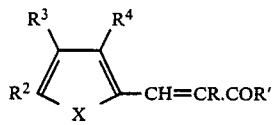

wherein X is —O— or —NH—; R, $R^2$, $R^3$, $R^4$, is H, $CH_3$, —CN, —$C_2H_5$ and OH, —$OCH_3$, —$OC_2H_5$; R' is selected from an alkyl, alkenyl, aryl or alkyl substituted aryl radical having 5-18 carbon atoms and the radical $OR^5$ where $R^5$ is an alkyl, alkenyl, aryl or alkyl substituted aryl radical having 6-18 carbon atoms.

11 Claims, No Drawings

ULTRAVIOLET RADIATION ABSORBING COMPOSITIONS

This is a continuation of co-pending application Ser. No. 06/817,501 filed on 1/9/86, now abandoned.

The present invention is directed to ultraviolet absorbing compositions comprising certain novel conjugated 2-substituted furan and pyrrole derivatives and blends which are useful as protective coatings, and to a method for protecting substrates against the harmful effects of actinic radiation. It is further directed to a process for making ultraviolet absorbing coating compositions. It is further directed to coating compositions having the capability of repelling insects.

Ultraviolet radiation absorbing coatings are useful in protecting substrates such as plastic resins against accelerated deterioration and the skin of warm blooded animals against severe erythema, edema, and blistering.

The present invention relates to novel sun-screen compositions and blends thereof which can be incorporated with waxes, oils, lacquers and soft resins in the preparation of furniture and auto polishes, cosmetics, sun tan oils and lotions, lipstick, hair treatments, skin formulations, and contact lenses. In particular the present invention relates to sunscreen compositions comprising an acceptable carrier having incorporated therein an effective amount (0.1–50% by weight) of a filtering agent for ultraviolet radiation selected from a compound having the general formula:

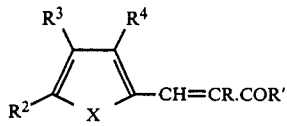

wherein X is —O— or —NH—, R, $R^2$, $R^3$ and $R^4$ is selected from —H; —$CH_3$; —CN; —$C_2H_5$; and OH, —$OCH_3$, —$OC_2H_5$, —OPh; R' is an alkyl or alkenyl, aryl and alkyl substituted aryl radical having 5-22 carbon atoms and —$OR^5$ wherein $R^5$ is an alkyl, alkenyl, aryl or alkyl substituted aryl radical having 1-22 carbon atoms. Of particular interest are furan compositions which are liquids and wherein R' is selected such that the derivative is liquid at room temperature such as the compound wherein R is H and R' is isoamyl which provides selective absorption in the 295–315 nm range as well as the 315–400 nm range. Such liquid compounds are of further interest in that they are expected to be insect repellents. In the case where insect repellency is not of interest compounds wherein the selection of R produces a solid such as n-amyl the stability is substantially enhanced and insect repellency is not needed. The ketone derivatives are particularly interesting for use as filtering agents for the prevention of erythema in that they provide intense protection in the UVB range as well as some protection in the tanning range. The compounds are present in the coating compositions as a solute and in the latter case as a solute in a pharmaceutically acceptable carrier provided that the selection of said carrier is such that the coating retains an absorbancy in the 290–400 nm range.

The compositions of the invention comprise the compounds in an amount effective to provide protection against the harmful effects of ultraviolet radiation. The amount or concentration of the compounds in the composition is such that when the composition is topically applied the desired protection is provided. The amount needed to provide the desired protection can vary with the characteristics of the compound that is its extinction coefficient or substantivity, the nature of the carrier, the source and intensity of the radiation and other well recognized variables. Suitable amounts can be readily determined by standard methods of dermatological testing. Preferably the UV filter compounds are incorporated in a carrier in an amount ranging from about 0.1% to about 50% by weight and usually in amounts ranging from 0.5 to 30% by weight.

Acceptable carriers include any vehicle or medium capable of incorporating the UV filter compound in a manner permitting uniform topical application. The term "pharmaceutically acceptable" is intended as a term of qualification in that the carrier should be dermatologically innocuous to warm blooded animals and cosmetically acceptable. The carrier may comprise a wax, oil or cream base material in which the agent can be held in a uniform dispersion for example as submicron size particles. Preferably the carrier comprises a suitable solvent or mixture of solvents capable of dissolving the UV filter compound to provide a concentration that is effective as a sunscreen agent when incorporated in the sunscreen formulation. Solvents which may be used include alcohols, ketones, hydrocarbon, chlorinated hydrocarbon, ethers, esters, polyethers, polyetherpolyols esters of polyols, and other special solvents such as dimethylsulfoxide, dimethylformamide and the like. Commercially available polyols of the preferred type include polyetherpolyol esters of fatty acids. Such solvents are considered useful only if they do not permanently interact with the furan filtering agents of the invention to shift the total effective absorption outside the 290–400 nm range.

The sunscreening compositions may be applied as a clear liquid or a lotion comprising a water-in-oil or oil-in-water emulsion. Either the oil or water base or both may be used as a carrier for the sun-screening compositions of the invention. The oil based materials and the water and oil base compositions will form a continuous film of the UV filtering compound. Such films also provide long-lasting protection against sun induced erythema. Sunscreening formulations are generally used in hot weather and at beaches where people enjoy bathing activities. It is therefore essential that the protective coating applied to the skin is not appreciably effected by water or perspiration. The compositions herein disclosed are included in a thin layer protective coating on the skin of warm blooded animals and provide long-lasting protection against erythema and do not decompose over long periods of exposure to sunlight.

The following examples serve as illustrations and are not meant to limit the invention. All parts and percentages are by weight unless otherwise specified.

The UV filtering compounds of the invention may be made by any acceptable synthetic technique but are readily obtained from commercially available materials such as furyl acrylate, furyl methacrylate, furyl ethacrylate and alkylesters thereof wherein the alkyl groups has 1-3 carbon atoms. The compounds of the invention are made either by direct condensation of a primary, secondary or tertiary alcohol having 5-18 carbon atoms or by transesterification of the ester with the higher molecular weight alcohol in the presence of an appropriate catalyst.

Furfurylidene and pyrollidene alkyl ketones are traditionally made by condensation of furfural or 2-pyrrolaldehyde with the appropriate ketone under typical Claisen-Schmidt condensation conditions and catalysts. The desired products may be separated from reaction mixtures using conventional separation techniques.

PREPARATION A

Furfurylidene n-amyl ketone

Into a 3-neck round bottom flask equipped with a thermometer, condenser and magnetic stirrer where placed 96 g (1.0 mol) furfural and 114 g (1.0 mol) 2-heptanone and cooled to 10° C. 33% sodium hydroxide solution (20 cc) where added rapidly to the solution which was kept below 60° C. in a ice bath for one hour. The reaction was ended by neutralization, excess ketone and furfural stripped at 5 torr and 23°–25° C. head temperature. The residue was purified by typical gas chromatographic techniques wherein 95.6 g (49.8%) was found to be 99.7% pure furfurylidene n-amyl ketone. Spectrophotometric analysis indicated a peak absorption at 314.9 nm and a K value of 129.1. Some residual furfural was present, however, this was reduced to 720 ppm by thorough water washing. Additional water washing and vacuum drying lowered the ketone content to 230 ppm and a furfural content to 530 ppm.

PREPARATION B

2-Ethylhexylfurylacrylate

Furylacrylic acid (23 g, 0.135 mol), 2-ethylhexanol (87.5 g, 0.67 mol) and 0.5 ml Tyzor ® (DuPont tetraisopropyltitanate) were mixed in a 3-neck round bottom flask equipped with a thermometer, condenser and high speed stirrer. The mixture was heated to 190° C. and held there with stirring until the theoretical 2.4 ml of water was distilled off at atmospheric pressure. The residual product was distilled at 134° C./0.5 torr yielding 33.0 g (92.6%) of 2-ethylhexylfuryl acrylate. A gas chromatagraphic analysis indicated the product was 97.1% pure. The material has peak absorption at 300.1 nm and a K of 98.3.

PREPARATION C

2-Ethylhexylfurylmethacrylate

In a procedure similar to that used in Preparation B, 76.0 g furylmethacrylic acid (0.5 mol), 130 g, 2-ethylhexanol (2 mols) and 2.4 g Tyzor ® were reacted and purified. The material has a peak absorption at 301.0 mm and a K of 94.6.

Use of the compounds of the invention can be demonstrated in lotion formulations which are topically applied to the surface of the skin. The following lotions can be applied to the skin surface of albino guinea pigs which are thereafter exposed to ultraviolate radiation in the range of 290–320 nm. Changes in the coloration of the skin surface such as redness and tanning is detected employing an apparatus described in U.S. Pat. No. 4,528,986. This apparatus is a device which employs the measurement of emitted green light having approximately 565 nm wavelength from the surfaces of red or brown skin areas. The use of such an apparatus permits a quantative assessment of the affects of treatment of skin inflammation or the extent of erythema and/or tanning following exposure to UV light.

The following lotions and creams will serve to illustrate but not limit those which can be used in the practice of the invention.

In general typical formulating techniques are well known to skilled formulators and usually require that the filtering agent be first added to the oil phase which is thereafter emulsified. With regard to Examples 1–4 all ingredients can be mixed together and stirred in conventional apparatus. With regard to Examples 5–8 composition I is usually heated to about 60° C. and formulation II is heated 65° C. II is then added slowly to I with moderate agitation. III is added cold while the resulting blend is permitted to cool to 50° C. and thereafter IV and V are added. Perfumes, antioxidants and stabilizers are added at room temperature. Any water lost during preparation is added to bring the composition to 100%.

The lotions are used by applying to the surface of the skin to permit an even coating after the aqueous phase is dissipated either through absorption or by evaporation.

| Example No. | Filtering Agent | Carrier Ingredients | Composition (% by Wt) | Appearance |
|---|---|---|---|---|
| 1 | Prep B |  | 4.58 | cloudy |
|  |  | Tween ® 20 polyethylene (20) sorbitan monolaurate | 10.0 | liquid |
|  |  | Ethanol (SD40) | 47.7 |  |
|  |  | Water | 37.74 |  |
|  |  |  | 100 |  |
| 2 | Prep A |  | 4.67 | clear |
|  |  | Tween 20 | 8.41 | liquid |
|  |  | Ethanol (SD40) | 48.6 |  |
|  |  | Water | 38.32 |  |
|  |  |  | 100 |  |
| 3 | Prep B |  | 4.58 | white |
|  |  | Tween 20 | 8.0 | cream |
|  |  | Tween ® 60 polyoxyethylene (20) sorbitan monostearate | 2.1 |  |
|  |  | Ethanol (SD40) | 47.7 |  |
|  |  | Water | 37.62 |  |
|  |  |  | 100 |  |
| 4 | Prep A |  | 4.58 | white |
|  |  | Tween 20 | 8.0 | lotion |
|  |  | Tween 60 | 2.1 |  |
|  |  | Ethanol (SD 40) | 47.7 |  |
|  |  | Water | 37.62 |  |

| Example No. | Filtering Agent | Carrier Ingredients | Composition (% by Wt) | Appearance |
|---|---|---|---|---|
| | | | 100 | |
| 5 | Prep A | | 5.0 | |
| | | I Arlamol ® E polyoxypropylene 15 stearyl ether | 7.0 | |
| | | Stearyl alcohol, Fallek Products | 2.5 | |
| | | Silicone oil, SF 96 (350 cps), General Electric | 1.0 | |
| | | Arlasolve ® 200 poe 20 isohexadecyl ether | 3.1 | |
| | | Brij ® 72 poe 2 stearyl ether | 3.9 | |
| | | II Water, deionized | 76.9 | |
| | | Carbopol ® 934, B. F. Goodrich | 0.2 | |
| | | III Sodium hydroxide (10% aqueous w/w) | 0.2 | |
| | | IV Dowicil ® 200, Dow Chemical | 0.1 | |
| | | V Herbal ® SL79-1224, PFW | 0.1 | |
| | | | 100.0 | |
| 6 | Prep B | | 2.5 | |
| | Prep A | | 2.5 | |
| | | I Stearyl alcohol, Fallek Products | 1.5 | |
| | | Silicone oil, 350 cps | 0.5 | |
| | | Tween ® 60 poe 20 sorbitan monostearate | 3.0 | |
| | | Span ® 60, sorbitan monostearate | 2.0 | |
| | | II Water, deionized | 87.4 | |
| | | Carbopol ® 934, B. F. Goodrich | 0.2 | |
| | | III Sodium hydroxide (10% aqueous w/w) | 0.2 | |
| | | IV Dowicil ® 200, Dow Chemical | 0.1 | |
| | | V Herbal ® SL79-1224, PFW | 0.1 | |
| | | | 100.0 | |
| 7 | Prep C | | 5.0 | |
| | | I Mineral Oil, Carnation Brand, Witco Chemical Company | 5.0 | |
| | | Stearyl alcohol, Fallek Products | 0.5 | |
| | | Brij ® 721 poe 21 stearyl ether | 2.0 | |
| | | Brij 72 poe 2 stearyl ether | 2.0 | |
| | | Silicone oil, SF-96, 350 cps, General Electric | 0.5 | |
| | | II Water, deionized | 84.5 | |
| | | Carbopol ® 940, B. F. Goodrich | 0.2 | |
| | | III Sodium hydroxide (10% aqueous w/w) | 0.2 | |
| | | IV Dowicil ® 200, Dow Chemical | 0.1 | |
| | | | 100.0 | |
| 8 | Prep A | | 2.5 | |
| | Prep C | | 2.5 | |
| | | I Petrolatum, Ultima Brand | 35.0 | |
| | | Brij 721 | 1.2 | |
| | | Brij 72 | 3.8 | |
| | | Silicone Oil, 350 cs. Ruger Chemical Company | 3.0 | |
| | | II Water, deionized | 51.1 | |
| | | Carbopol ® 934, B. F. Goodrich | 0.4 | |

-continued

| Example No. | Filtering Agent | Carrier Ingredients | Composition (% by Wt) | Appearance |
|---|---|---|---|---|
| | | III Sodium hydroxide (10% aqueous w/w) | 0.4 | |
| | | IV Dowicil ® 200, Dow Chemical | 0.1 | |
| | | | 100.0 | |
| 9 | Aerosol Hairdressing Prep A | | 5.0 | |
| | | Decaglycerol monolaurate | 2.0 | |
| | | Polypropylene (200) monooleate | 3.0 | |
| | | Ethoxylated (10) lanolin alcohols | 1.0 | |
| | | Propylene glycol | 2.0 | |
| | | Ethyl alcohol, anhydrous | 39.5 | |
| | | Protein polypeptide (20% alcoholic) | 1.2 | |
| | | Isopropyl myristate | 1.3 | |
| | | Propellant 11 | 15.0 | |
| | | Propellant 12 | 30.0 | |
| | | Water | q.s. | |

Procedure for Formula: Dissolve all ingredients in slightly warmed ethylalcohol, avoiding loss of the alcohol, add the water, and agitate well to disperse any haze. Filter the concentrate and fill into aerosol containers. Add propellants.

| | | | | |
|---|---|---|---|---|
| 10 | Formula for Creamy Type Lipstick Base Prep B | | 5 | |
| | | Carnauba wax | 3 | |
| | | Candelilla wax | 7 | |
| | | Ozokerite | 3 | |
| | | Beeswax | 7 | |
| | | Lanolin | 10 | |
| | | Castor oil | 60 | |
| | | Isopropyl myristate | 5 | |
| | | Perfume | q.s. | |
| 11 | Water-In-Oil (W/O), Detergent Resistant, Liquid Auto Polish | | | |
| | Part A | 2.00% Durmont 500 Montan Wax | (Dura Commodities) | |
| | Part B | 0.75% DC 530 Silicone Fluid | Dow Corning | |
| | | 4.25% DC 531 Silicone Fluid | | |
| | | 1.50% SPAN ® 80 | | |
| | | 10.00% Kerosene | | |
| | | 16.50% Stoddard Solvent | | |
| | | 5.0% Preparation C | | |
| | Part C | 10.00% Kaopolite SFO | (Kaopolite) | |
| | Part D | 50.00% Water | | |

Method of Preparation:
1. Melt wax in Part A (85–90° C.)
2. Add Part B ingredients to melted wax and stir to blend well. Return temperature to 85–90° C.
3. Add Part C to Part A/Part B blend and mix until uniform with medium agitation. Keep temperature in the 85–90° C. range.
4. Heat Part D to 95° C. and slowly add to the blend with high speed stirring until emulsion is obtained.
5. Cool to 40–45° C. with continuous stirring.
6. Homogenize.

| | | | | |
|---|---|---|---|---|
| 12 | Neutral Base Lacquer | | | |
| | Materials | | Pounds | |
| | Urethane 60% N.V. | | 32 | |
| | Long oil alkyd 60% N.V. | | 352 | |
| | Triton X-45 | | 7.5 | |
| | Nuxtra Calcium 6% | | 12 | |
| | Bentone Jell 8% | | 28 | |

Disperse the bentone jell under high speed cowles and add:

| | | |
|---|---|---|
| Preparation B | | 16 |
| Low odor mineral spirits | | 85 |
| Cyclodex cobalt 6% | | 3 |

| Example No. | Filtering Agent | Carrier Ingredients | Composition (% by Wt) | Appearance |
|---|---|---|---|---|
| | JK 270-70% | | 76 | |
| | Water | | 205 | |
| | Anti skin | | 2 | |
| | Viscosity: 80-85 KU | | | |
| | W/G: 7.84 | | | |
| | 60° Gloss: 85 | | | |
| | SAG: 6 ml | | | |
| 13 | O/W Paraffin Wax Emulsion | | | |
| | Part A | 50% Paraffin wax | | |
| | | 5% SPAN 60/TWEEN 60 (50/50) | | |
| | | 5% Preparation A | | |
| | Part B | 40% Water | | |
| | Method of Preparation: | | | |
| | 1. | Melt Part A ingredients together and heat to 80° C. | | |
| | 2. | Heat Part B to 85° C. | | |
| | 3. | Add Part B to Part A slowly with moderate agitation until inversion occurs. Add remaining water rapidly. | | |
| | 4. | Cool in cold water bath with slow agitation to approximately 35° C. | | |
| 14 | O/W Soft Microcrystalline Wax Emulsion | | | |
| | Part A | 30% Microcrystalline wax (Ultraflex Amber Wax-Petrolite Corp.) | | |
| | | 30% SPAN 60/TWEEN 60 (78/22) | | |
| | | 5% Preparation B | | |
| | Part B | 62% Water | | |
| | Method of Preparation: | | | |
| | 1. | Melt together Part A ingredients and heat to 80-90° C. | | |
| | 2. | Heat Part B to boiling. | | |
| | 3. | Add Part B to Part A slowly with moderate agitation until inversion occurs. Add remaining water rapidly. | | |
| | 4. | Remove from heat and cool to room temperature without stirring. | | |
| 15 | O/W Carnauba Wax Emulsion | | | |
| | Part A | 10% Carnauba wax | | |
| | | 3% TWEEN 80 | | |
| | | 5% Preparation C | | |
| | Part B | 82% Water | | |
| | Method of Preparation: | | | |
| | 1. | Melt Part A ingredients together and heat to 95° C. and hold. | | |
| | 2. | Heat Part B to boiling. | | |
| | 3. | Add Part B to Part A slowly with moderately fast stirring until inversion occurs. Add remaining water rapidly. | | |
| | 4. | Remove emulsion from heat and cool rapidly with stirring. | | |

What is claimed is:

1. A method for protecting a substrate against the harmful effects of ultraviolet radiation in the 290-400 nm range which comprises topically applying a composition as a clear liquid or lotion having uniformly dispersed therein an amount effective to provide protection against the harmful effects of ultraviolet radiation a compound having the formula:

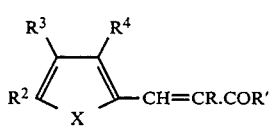

where X is —O— or NH—; R, $R^2$, $R^3$, $R^4$ is —H, —$CH_3$, —$C_2H_5OH$, —$OCH_3$, —$OC_2H_5$, —OPh; R' is selected from the group consisting of an alkyl, an alkenyl, an aryl, or alkyl substituted aryl radical having 5-22 carbon atoms or $OR^5$ where $R^5$ is an alkyl, alkenyl, aryl, or alkyl substituted aryl radical having 1-22 carbon atoms.

2. A method of claim 1 wherein said compound is incorporated in said composition in an amount ranging from about 0.1 to about 50% by weight.

3. A method of claim 2 wherein said compound is incorporated in said composition in an amount ranging from about 1 to about 10% by weight.

4. A method of claim 1 wherein said compound is dissolved in said clear liquid or lotion.

5. A method of claim 1 wherein said carrier is an aqueous emulsion.

6. A method of claim 1 wherein said substrate is the skin of a warm-blooded animal.

7. A sunscreen composition which absorbs in the 290-400 nm range comprising a pharmaceutically acceptable clear liquid or lotion carrier having uniformly dispersed therein 0.1-50% by weight of a UV filter compound of the formula:

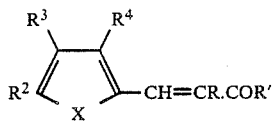

wherein X is —O— or —NH—; R, R², R³, R⁴ is —H, —CH₃, —C₂H₅ and —OH, —OCH₃, —OC₂H₅, —OPh; R' is selected from the group consisting of an alkyl, alkenyl, aryl or alkyl substituted aryl radical having 5-22 carbon atoms and the radical OR⁵ where R⁵ is an alkyl, alkenyl, aryl or alkyl substituted aryl radical having 1-22 carbon atoms whereby said carrier and said UV filter do not interact to shift the effective absorption outside the 290-400 nm range.

8. A composition of claim 7 wherein R is H and R' is alkyl radical having 5 carbon atoms.

9. A composition of claim 8 wherein R' is isopentyl.

10. A composition of claim 7 wherein R⁵ is 2-ethylhexyl.

11. A composition of claim 7 containing a mixture of furfurylidene n-amyl ketone with 2-ethylhexylfurylacrylate or 2-ethylhexylfurylmethacrylate.

* * * * *